United States Patent
Boraiah et al.

(10) Patent No.: US 8,109,943 B2
(45) Date of Patent: Feb. 7, 2012

(54) SYSTEMS AND METHODS FOR SUTURE ANCHOR DEPLOYMENT

(75) Inventors: Sreevathsa Boraiah, Valhalla, NY (US); Robert Michael Koch, New York, NY (US)

(73) Assignee: Gordian Surgical, LLC, Stamford, CT (US)

( * ) Notice: Subject to any disclaimer, the term of this patent is extended or adjusted under 35 U.S.C. 154(b) by 481 days.

(21) Appl. No.: 12/384,927

(22) Filed: Apr. 10, 2009

(65) Prior Publication Data

US 2010/0262166 A1 Oct. 14, 2010

(51) Int. Cl.
*A61B 17/10* (2006.01)

(52) U.S. Cl. .................................... 606/139

(58) Field of Classification Search ............ 606/72, 606/73, 139–150, 213, 232, 153, 300; 623/23.72
See application file for complete search history.

(56) References Cited

U.S. PATENT DOCUMENTS

| | | | | |
|---|---|---|---|---|
| 4,553,543 A * | 11/1985 | Amarasinghe | ................. | 606/148 |
| 5,320,632 A * | 6/1994 | Heidmueller | ................. | 606/144 |
| 5,364,408 A | 11/1994 | Gordon | | |
| 5,372,588 A | 12/1994 | Farley et al. | | |
| 5,374,275 A * | 12/1994 | Bradley et al. | ................. | 606/144 |
| 5,403,328 A * | 4/1995 | Shallman | ................. | 606/144 |
| 5,470,338 A | 11/1995 | Whitfield et al. | | |
| 5,496,332 A * | 3/1996 | Sierra et al. | ................. | 606/139 |
| 5,527,321 A | 6/1996 | Hinchliffe | | |
| 5,540,704 A | 7/1996 | Gordon et al. | | |
| 5,562,688 A * | 10/1996 | Riza | ................. | 606/148 |
| 5,573,540 A | 11/1996 | Yoon | | |
| 5,575,800 A * | 11/1996 | Gordon | ................. | 606/144 |
| 5,586,986 A | 12/1996 | Hinchliffe | | |
| 5,700,273 A * | 12/1997 | Buelna et al. | ................. | 606/148 |
| 5,860,991 A * | 1/1999 | Klein et al. | ................. | 606/144 |
| 6,074,404 A * | 6/2000 | Stalker et al. | ................. | 606/144 |
| 6,461,366 B1 * | 10/2002 | Seguin | ................. | 606/144 |
| 6,491,707 B2 * | 12/2002 | Makower et al. | ................. | 606/157 |
| 6,743,241 B2 | 6/2004 | Kerr | | |
| 6,911,034 B2 * | 6/2005 | Nobles et al. | ................. | 606/144 |
| 6,960,164 B2 | 11/2005 | O'Heeron | | |
| 7,273,489 B2 * | 9/2007 | Boudjemline | ................. | 606/213 |
| 7,449,024 B2 * | 11/2008 | Stafford | ................. | 606/144 |
| 7,824,419 B2 * | 11/2010 | Boraiah | ................. | 606/144 |
| 7,875,041 B2 * | 1/2011 | Mikkaichi et al. | ................. | 606/144 |
| 7,967,842 B2 * | 6/2011 | Bakos | ................. | 606/232 |
| 2002/0045908 A1 * | 4/2002 | Nobles et al. | ................. | 606/144 |

(Continued)

OTHER PUBLICATIONS

USPTO Office Action dated Dec. 31, 2008 regarding U.S. Appl. No. 11/673,280, 6 pages.
USPTO Office Action dated Apr. 21, 2009 regarding U.S. Appl. No. 11/673,280, 6 pages.

(Continued)

*Primary Examiner* — Melanie Tyson
*Assistant Examiner* — Son Dang
(74) *Attorney, Agent, or Firm* — Ryan Kromholz & Manion, S.C.

(57) ABSTRACT

Provided are systems and methods for suture anchor deployment. A system according to the present invention is a trocar system that includes a cannula assembly and an obturator assembly, the cannula assembly providing a needle assembly and the obturator assembly providing a needle actuation mechanism. The obturator assembly may be at least partially inserted into the cannula assembly and arranged to operatively couple the needle actuation mechanism to the needle assembly. The needle assembly includes at least one needle, each needle having disposed near its distal tip a suture anchor. A method according to the present invention includes steps for deploying and/or depositing at least one suture anchor in or through an organ of the human body.

21 Claims, 14 Drawing Sheets

U.S. PATENT DOCUMENTS

| | | |
|---|---|---|
| 2003/0105473 A1 | 6/2003 | Miller |
| 2003/0181924 A1 | 9/2003 | Yamamoto et al. |
| 2005/0149066 A1 | 7/2005 | Stafford |
| 2007/0213757 A1 | 9/2007 | Boraiah |

OTHER PUBLICATIONS

USPTO Office Action dated Aug. 18, 2009 regarding U.S. Appl. No. 11/673,280, 10 pages.

* cited by examiner

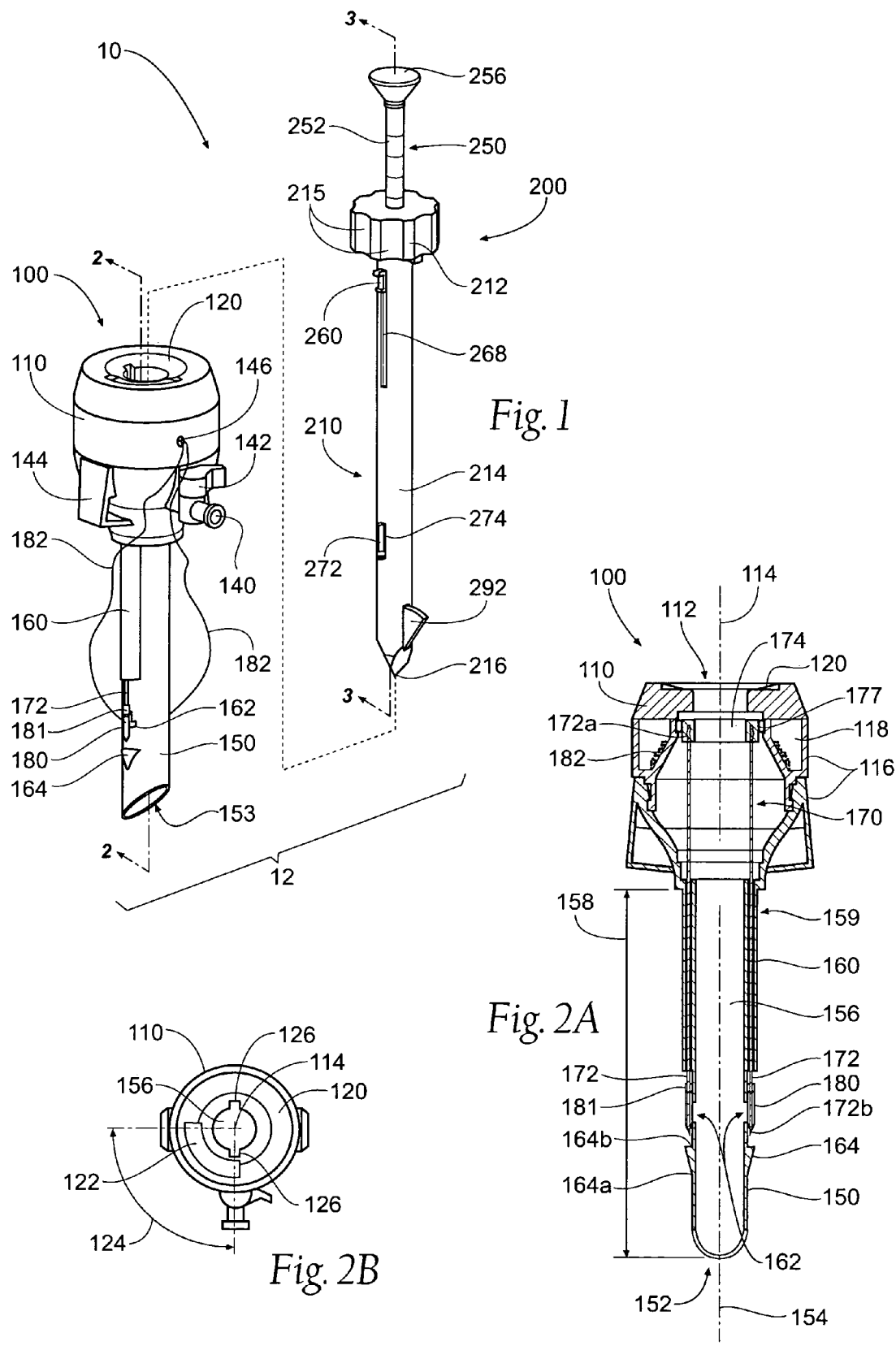

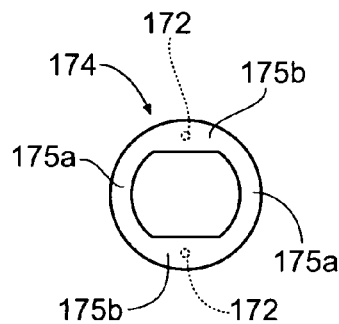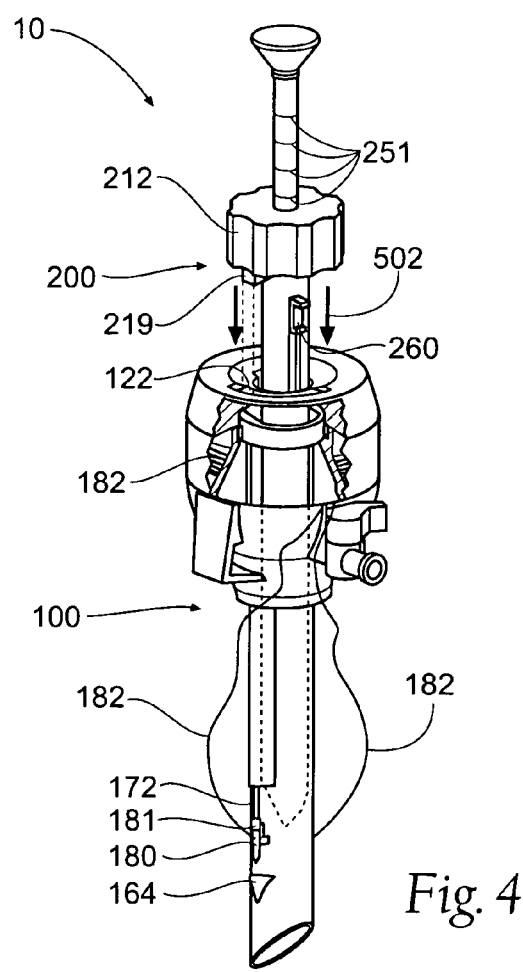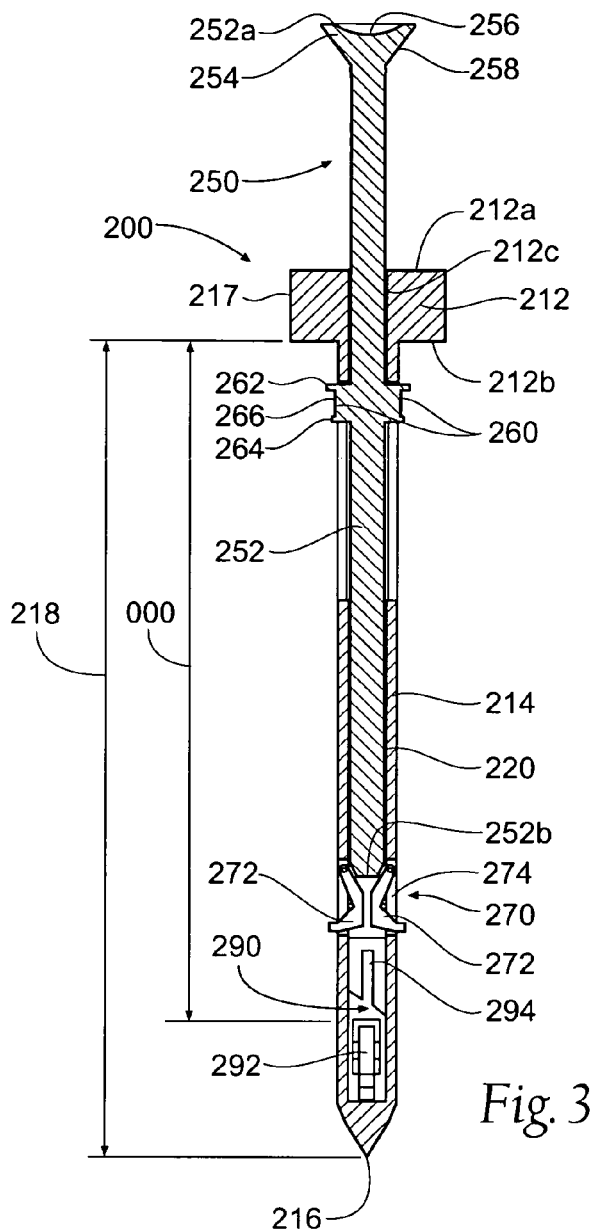

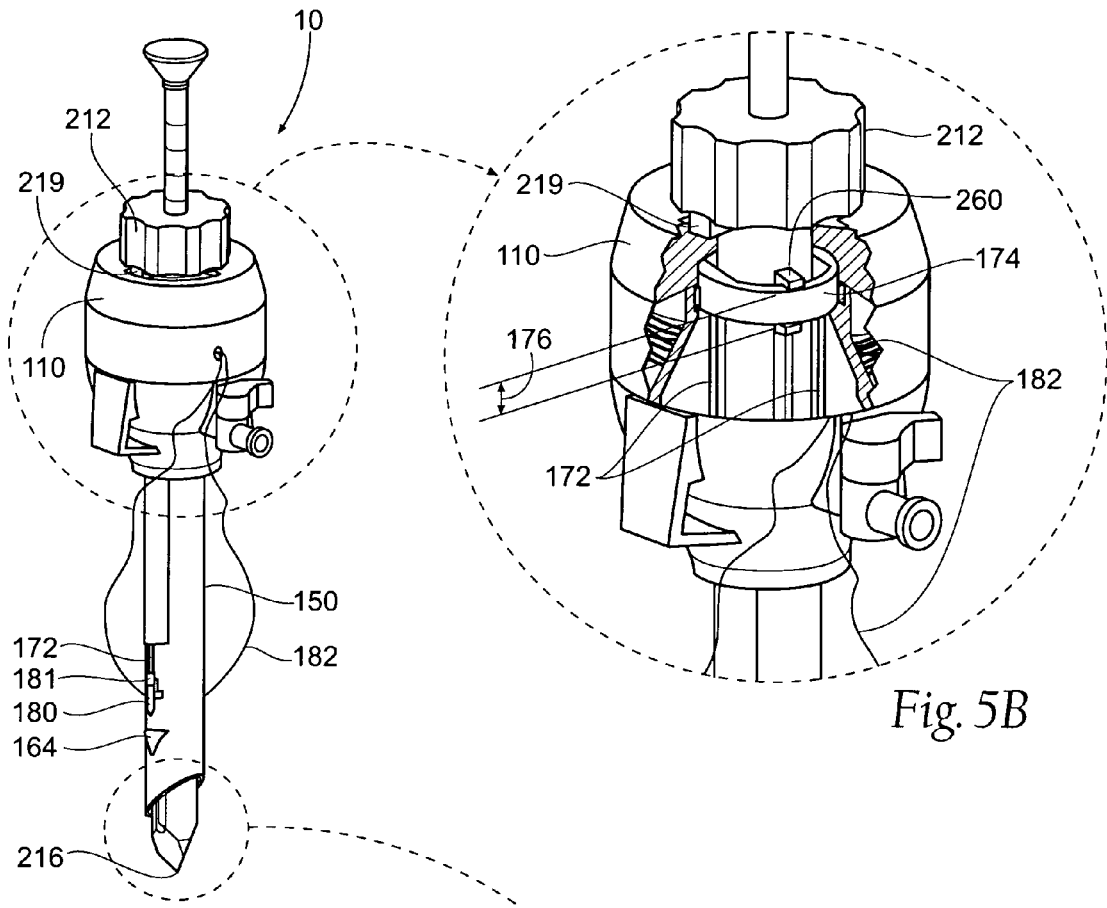
Fig. 5A
Fig. 5B
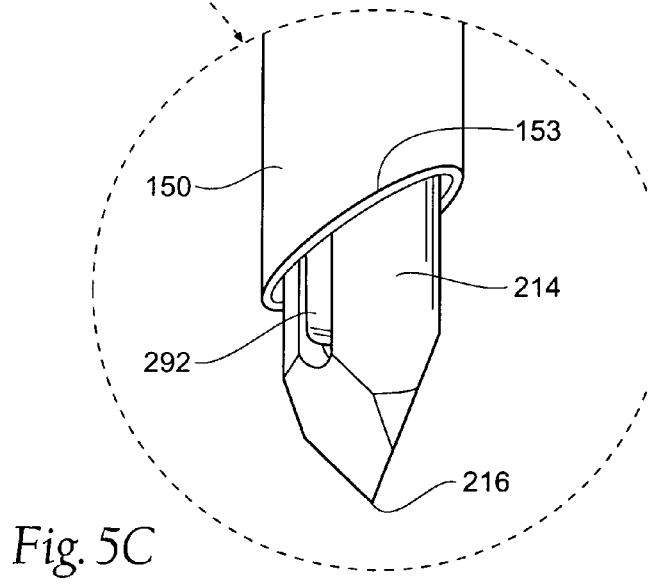
Fig. 5C

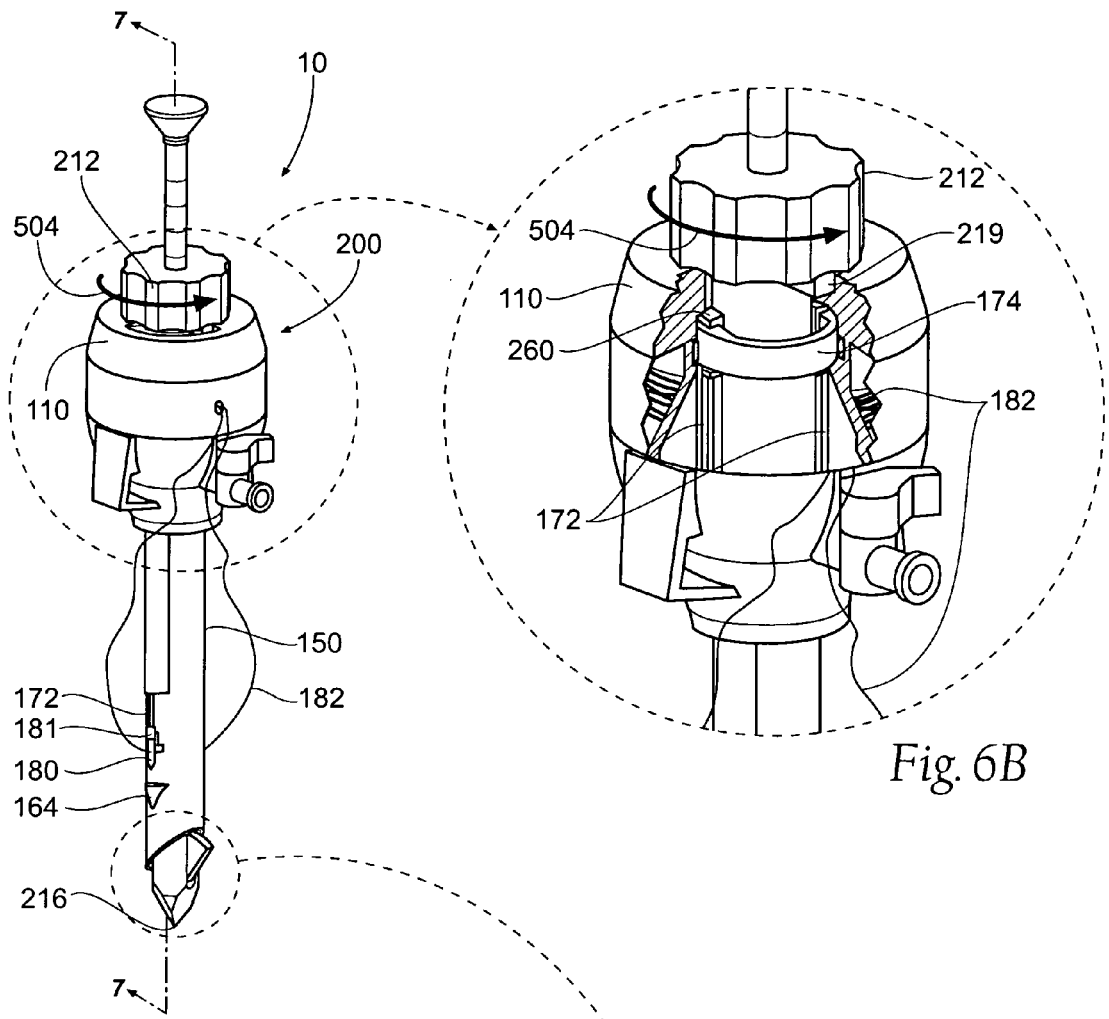
Fig. 6A
Fig. 6B
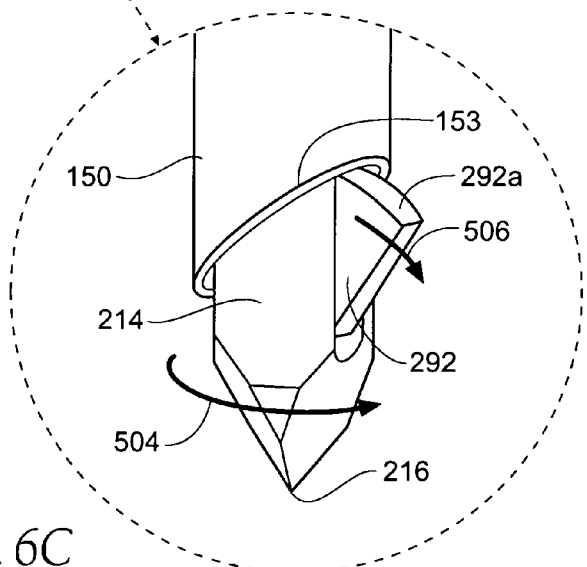
Fig. 6C

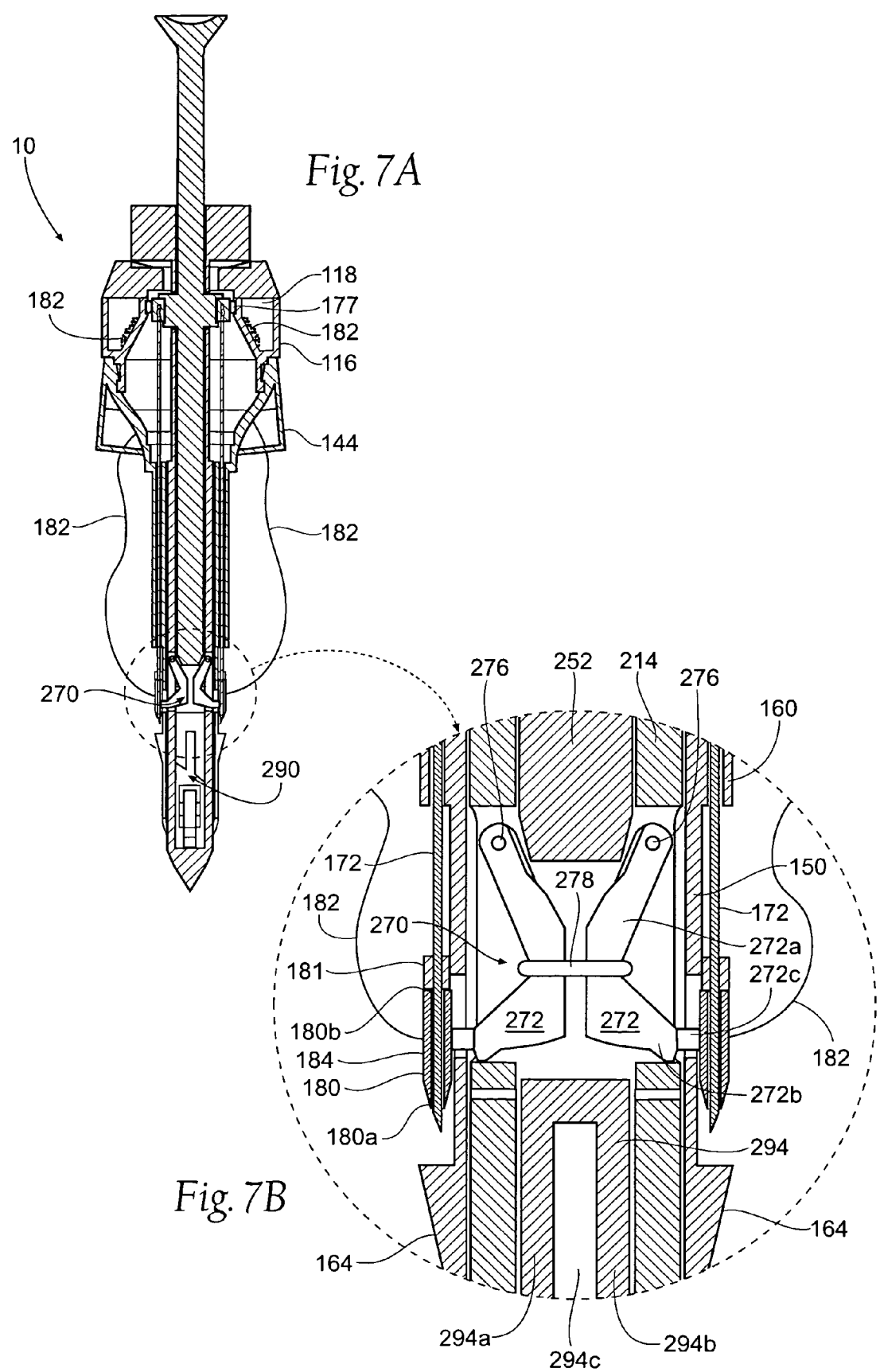

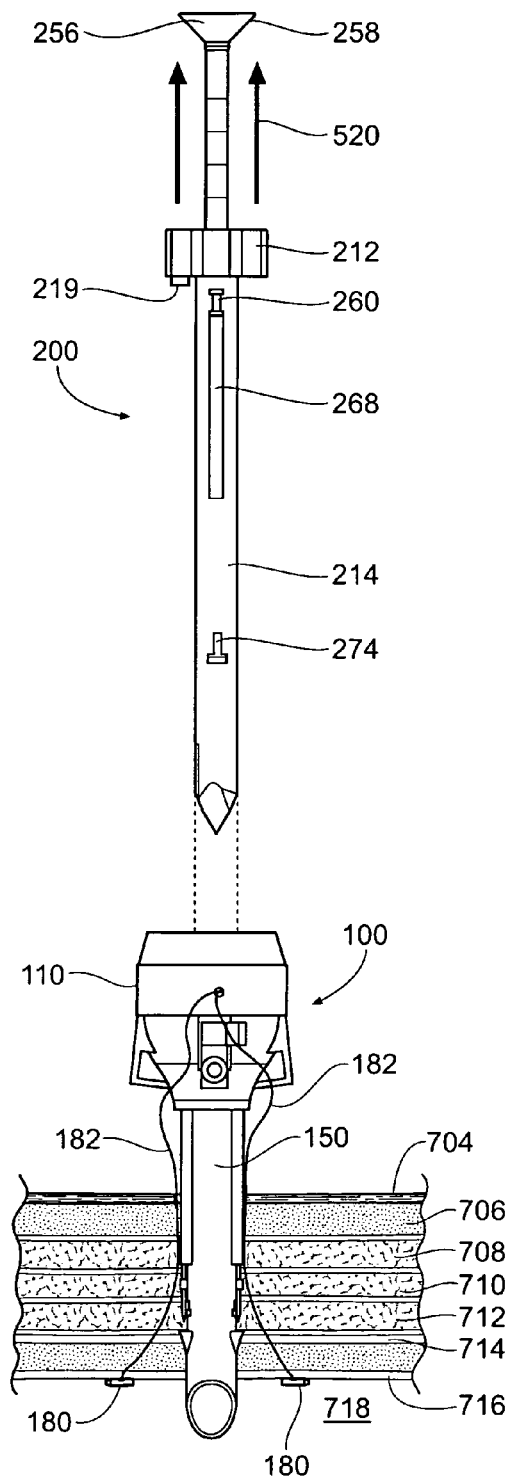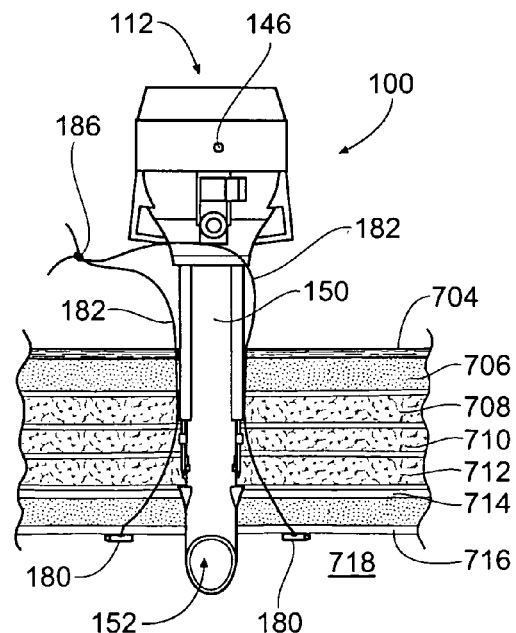
Fig. 17
Fig. 18

SYSTEMS AND METHODS FOR SUTURE ANCHOR DEPLOYMENT

BACKGROUND OF THE INVENTION

Endoscopic surgery is a significant method of performing surgical operations and has become the surgical procedure of choice due to its patient care advantages over "open surgery." A particular type of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves decreased incidents of post-operative abdominal adhesions, decreased tissue damage, decreased post-operative pain, and enhanced cosmetic results. Laparoscopic surgery consequently permits the patient to return to normal activity in a short period of time.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then pierced or penetrated with two or more devices known as trocars. A trocar includes a housing assembly, a piercing element referred to as an obturator, and a shaft that extends therebetween. A cannula assembly, having a cylindrical port element, is slid over the shaft. After insertion of the trocar through the abdominal wall of the patient, the obturator is removed by the surgeon while leaving the port element protruding through the abdominal wall. The port element may be fixed in place by using a fascia device, and laparoscopic surgical instruments can then be inserted through the port element to view internal organs and to perform surgical procedures.

Notwithstanding the advantages afforded by laparoscopic surgery, such technique has associated disadvantages. Specifically, the puncture wounds created within the body by the surgeon to gain access to the surgical site are often difficult and time-consuming to close, and can place great demands on the surgeon. Such tasks are made even more difficult when laparoscopic surgery is performed upon obese patients where there is a relatively deep puncture wound formed through a relatively small puncture site or incision. Indeed, the puncture site frequently needs to be enlarged following the laparoscopic procedure to ensure that the site is closed at the interior abdominal wall. In addition, many laparoscopic closure devices are incapable of deploying a suture a sufficient distance about the puncture site to fashion an appropriate closure. Such limited distance fails to sufficiently approximate the peritoneum and fascia surrounding the puncture site sufficiently to form an adequate closure.

One laparoscopic device is that described in U.S. Pat. No. 6,743,241 by Stephen Kerr, entitled, "Laparoscopic Port Site Fascial Closure Device." The stated device allows a surgeon to selectively deploy needles for positioning and stitching a suture across the puncture site that can ultimately be withdrawn from the puncture wound. Although the stated device has allowed for the deploying of a suture without the enlargement of the puncture site. The stated device also has associated disadvantages. In order to utilize the stated device the obturator and the cannula must be removed from the puncture site. This removal can cause temporary loss of the puncture site and/or some difficulty in the reinsertion of another cannula that is associated with the closing device. The removal of the first cannula also has time loss associated therewith.

Another disadvantage associated with the stated device is the inability to determine the extent of the penetration of the suturing needles into the peritoneum and fascia. Not knowing the penetration depth and the relation thereof to the thickness of the peritoneum and the fascia can result in a poor suture that may partially or fully open.

In addition, the stated device is use limited. The stated device is utilized solely for closure of a penetrated site and can only be used after there is no longer surgical use for the penetrated site and a decision is made to close the site.

Thus, there is a need for an improved laparoscopic technique and device for laparoscopic fascial closure that overcomes the above-stated disadvantages.

SUMMARY OF THE INVENTION

The present invention provides an improved technique and device for deploying suture anchors adapted for closure of a puncture into or through an organ of a human body.

An embodiment of the present invention includes a system for deploying a suture anchor, the system including a cannula assembly and a needle actuation mechanism. The cannula assembly includes a port element defining an open proximal port end and a distal portion opposite the proximal port end. A cannula shaft extends from the distal portion of the port element to an open distal cannula end. A first needle is at least partially longitudinally movable with respect to the cannula shaft, and a first suture anchor is removably, preferably passively, coupled to the first needle. A needle actuation mechanism is at least partially longitudinally movable with respect to the cannula shaft.

According to an aspect of the present invention, the system may further include an obturator assembly comprising an obturator housing including an obturator shaft at least partially insertable into and completely removable from the open proximal port end, wherein when the obturator shaft is operatively inserted into the cannula assembly, a first longitudinal movement of the needle actuation mechanism results in a corresponding second longitudinal movement of at least a first portion of the first needle.

According to another aspect of an embodiment of the present invention, the port element may include a top surface at the open proximal port end. The top surface may substantially surround a port aperture formed along a port longitudinal axis. The port aperture may be substantially circular in cross-section and may further include a yoke channel extending radially therefrom. The top surface may further include a rotational guide slot formed about the port longitudinal axis through a guide slot angle. The guide slot angle may be about ninety degrees. The port element may include a port housing substantially surrounding a hollow port cavity, and may also include a pair of retraction handles. The port housing may include an insufflation port in fluid communication with the port aperture, a stopcock operatively disposed to open and close the insufflation port, and a suture thread port in fluid communication with the hollow port cavity from external the housing.

According to still another aspect of an embodiment according to the present invention, the cannula shaft may have a substantially circular cross-section formed about a cannula longitudinal axis along a majority of a cannula shaft length. The open distal cannula end may include an ellipse formed in a plane provided at an acute ellipse angle measured distally from the open distal cannula end with respect to the cannula longitudinal axis. The ellipse angle may be an angle of between about twenty degrees and about seventy-five degrees. The cannula shaft may include a cannula throughbore-formed through the cannula shaft length about the cannula longitudinal axis. The cannula assembly may further include a flaring port extending radially outwardly from the cannula throughbore through the cannula shaft. The cannula shaft may also include a first needle fairing disposed on an outer surface of the cannula shaft. The needle fairing preferably slopes radially outwardly from the outer surface from a fairing distal end to a fairing proximal end. The cannula assembly may further include a longitudinal needle sheath disposed on the cannula shaft, where the sheath is positioned substantially parallel to the cannula longitudinal axis.

According to yet another aspect of an embodiment according to the present invention, a system may further include a needle flaring mechanism adapted to guide the first needle radially outwardly from the cannula shaft.

According to a further aspect of an embodiment according to the present invention, a system may further include a position indication mechanism. The position indication mechanism may include a wedge member pivotally mounted to an obturator shaft. The mechanism may also include a resilient wedge biasing member adapted to apply a wedge bias force to the wedge member forcing the wedge member radially outwardly from the obturator shaft. Also, a wedge retractor may be adapted to selectively overcome the wedge bias force to retract the wedge at least substantially into the obturator shaft. The position indication mechanism may further or alternatively comprise a plurality of depth markers disposed on an outer surface of said cannula shaft.

According to an embodiment of a method according to the present invention, a method of at least substantially closing an opening in a layer of an organ of a human body is provided. The method includes the step of providing a system, where the system comprises a housing formed about a longitudinal axis, a first needle longitudinally slidably supported on the housing, a first suture anchor disposed on the first needle, and a first suture thread coupled to the first suture anchor. The method also includes the steps of inserting at least a portion of the system into a portion of a layer of an organ of a human body and extending the first needle until the first suture anchor has penetrated the layer of the organ to a first depth. The method further comprises the steps of withdrawing the first needle from the layer, withdrawing the system from the layer, and at least substantially closing an opening in the layer using the first suture thread.

The providing step of a method according to the present invention may include providing a system that is a trocar system comprising a cannula assembly and an obturator assembly. The cannula assembly may include a port element defining an open proximal port end, the port element having a distal portion opposite the proximal port end. The cannula assembly may further include a cannula shaft extending from the distal portion of the port element to an open distal cannula end, wherein the first needle is at least partially longitudinally movable with respect to the cannula shaft. The obturator assembly provided may include an obturator housing including an obturator shaft and a needle actuation mechanism at least partially longitudinally movable with respect to the obturator shaft. The obturator shaft may be at least partially insertable into and completely removable from the open proximal port end, wherein when the obturator shaft is operatively inserted into the cannula assembly, a first longitudinal movement of the needle actuation mechanism results in a corresponding second longitudinal movement of at least a first portion of the first needle.

A method according to the present invention may further comprise the steps of withdrawing the obturator assembly from the cannula assembly and withdrawing the cannula assembly from the layer.

The provided system for performing the method may include a second needle longitudinally slidably supported on the housing, a second suture anchor disposed on the second needle, and a second suture thread coupled to the second suture anchor, wherein the method may further include the steps of extending the second needle until the second suture anchor has penetrated the layer of the organ to a second depth and withdrawing the second needle from the layer, wherein said at least substantially closing step further comprises using the second suture thread.

In a method according to the present invention, the withdrawing of the cannula assembly step may be performed after the withdrawing of the obturator assembly step.

In a method according to the present invention, the step of extending the first needle may include the step of extending the first needle to engage the layer of the organ at a needle bite distance measured from an outer surface of the housing at least substantially perpendicular to the longitudinal axis, wherein prior to the step of extending the first needle, the first needle is proximate and in a noncontacting relationship with the layer. The needle bite distance may be at least five millimeters and is preferably about 7.5 millimeters.

BRIEF DESCRIPTION OF THE DRAWINGS

FIG. 1 is a perspective view of an embodiment of a system for the deployment of suture anchors according to the present invention.

FIG. 2A is a cross-section view taken along line 2-2 of FIG. 1.

FIG. 2B is a top plan view of a needle engagement ring according to the present invention.

FIG. 2C is a top plan view of a cannula assembly according to the present invention.

FIG. 3 is a cross-section view taken along line 3-3 of FIG. 1.

FIG. 4 is a partial cutaway perspective view of the embodiment of FIG. 1 in a partially inserted state.

FIG. 5A is a perspective view of the embodiment of FIG. 1 in an inserted, disengaged state.

FIG. 5B is a partial cutaway view of the embodiment of FIG. 5A.

FIG. 5C is an enlarged view of a portion of the embodiment of FIG. 5A.

FIG. 6A is a perspective view of the embodiment of FIG. 1 in an inserted, engaged state.

FIG. 6B is a partial cutaway view of the embodiment of FIG. 6A.

FIG. 6C is an enlarged view of a portion of the embodiment of FIG. 6A.

FIG. 7A is a cross-section view taken along line 7-7 of FIG. 6A.

FIG. 7B is an enlarged cross-section view of a portion of FIG. 7A.

FIG. 17 is a front elevation view of a ninth step of a method according to the present invention.

FIG. 18 is a front elevation view of a tenth step of a method according to the present invention.

DESCRIPTION OF THE PREFERRED EMBODIMENT

Figure 8:
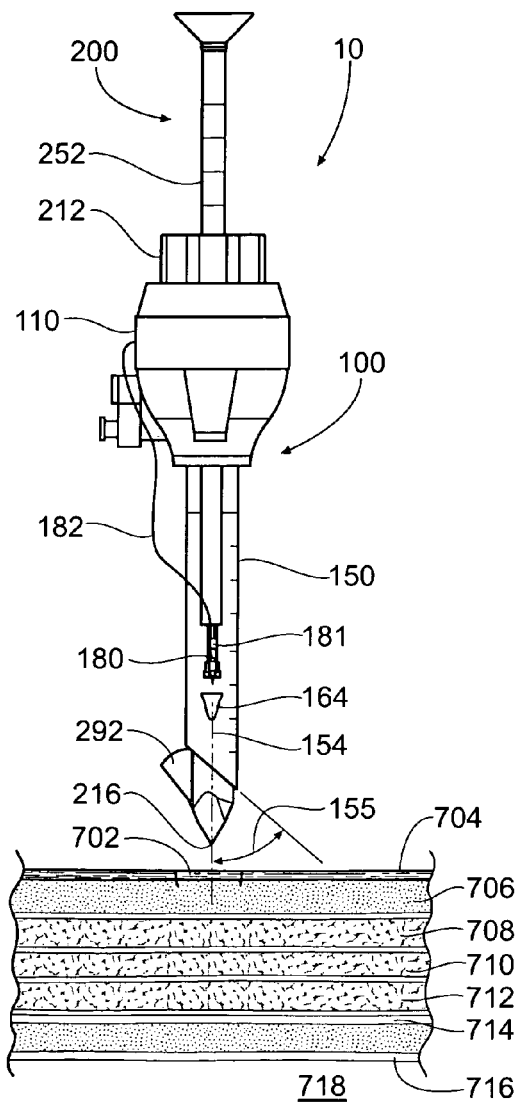
FIG. 8 is a right elevation view of a first step of a method according to the present invention.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Turning now to the figures, FIG. 1 depicts a first embodiment 10 of a suture anchor deployment system according to the present invention. The system 10 generally comprises a trocar system 12 that includes a cannula assembly 100 and an obturator assembly 200. The cannula assembly 100 can be seen in further detail with reference also to FIGS. 2A, 2B, and 2C. The cannula assembly 100 generally includes a port element 110 coupled to a cannula shaft 150, the port element 110 defining an open proximal port end 112 and the cannula shaft 150 defining an open distal cannula end 152. The cannula shaft 150 is formed about a cannula longitudinal axis 154, which is preferably coaxial with a port longitudinal axis 114 about which the port element 110 is formed. A cannula throughbore 156 extends, preferably at least substantially uninterruptedly, through the open proximal port end 112, through the port element 110, through the cannula shaft 150 and through the open distal cannula end 152, preferably coaxial to the longitudinal axes 114, 154. Alternatively, a deflation check valve (not shown), as is known in the art, may be operatively disposed in the cannula throughbore 156, the check valve operating to substantially interrupt the cannula throughbore 156 to, for example, prevent deflation of an insufflated abdomen. The port element 110 includes a port element housing 116, at least substantially enclosing a substantially hollow port cavity 118. The port element housing 116 has a top surface 120 generally surrounding, perhaps generally funneling towards, the cannula throughbore 156. As can be seen more clearly in FIG. 2B, the top surface 120 may include a rotational guide slot 122 formed into the top surface 120, through a desired guide slot angle 124, such as about ninety degrees, measured about the port longitudinal axis 114. Extending radially from the cannula throughbore 156 is one or more yoke channels 126. Where more than one yoke channel 126 is used, the yoke channels 126 may be evenly spaced about the circumference of the cannula throughbore 156.

The cannula shaft 150 is preferably a tubular shaft extending axially from a distal portion of the port element 110. The cannula shaft 150 extends along a cannula shaft length 158, terminating at the open distal cannula end 152. The open distal cannula end 152 is preferably formed as a planar ellipse 153 disposed at a desired ellipse angle 155, such as between about twenty degrees and about seventy-five degrees, and more preferably about forty-five degrees, which is measured relative to the cannula longitudinal axis 154. As explained in further detail below, the angled open distal cannula end 152 may aid in the controlled deployment of trocar position indication mechanism 290, if included. The cannula shaft 150 is preferably substantially cylindrical, extending around the cannula throughbore 156.

The cannula assembly 100 further includes a needle assembly 170. The needle assembly 170 includes at least one, but preferably, a plurality of needles 172, each needle having a captured end 172a and a free end 172b, wherein the free end 172b includes a pointed tip 172c. The captured end 172a of the needle 172, or another portion of the needle 172, if desired, is coupled to a needle engagement ring 174. The needle engagement ring 174 is preferably at least partially contained by the port element housing 116. Disposed between the port element housing 116 and the needle engagement ring 174 is an annular friction ring 177, which provides at least some frictional resistance to rotational movement of the needle engagement ring 174 about the port longitudinal axis 114. The needle engagement ring 174 is at least substantially longitudinally stationary with respect to the needles 172. That is, if the needle engagement ring 174 is forced in a longitudinal direction (such as the direction 510 in FIG. 12A), the needles 172, or portions thereof to which the needle engagement ring 174 is coupled, are generally forced in the same direction 510, traveling substantially, if not completely, the entire longitudinal distance that the needle engagement ring 174 travels. The captured end 172a of each needle 172 may be anchored to the needle engagement ring 174 in any number of ways, such as by adhesive, by mechanical engagement, or by known overmolding techniques.

Coupled to at least one, but preferably each, needle 172, preferably closer to the needle free end 172b than the needle captured end 172a, is a suture anchor 180. The suture anchor 180 is preferably generally tubular and bullet-shaped, having a narrower distal end 180a than proximal end 180b. The suture anchor 180 may be at least partially frictionally engaged about the needle 172. A suture anchor stop 181 may be provided relatively permanently coupled to the needle 172, proximal to the suture anchor 180, to prevent movement of the anchor 180 in the proximal direction. The suture anchor stop 181 preferably surrounds the needle 172 in at least one location and has a diameter measured orthogonal to the longitudinal needle 172 that is not greater than a similarly measured diameter of the suture anchor 180. Coupled to the suture anchor 180 is a suture thread 182. The suture thread 182 preferably extends through a sidewall 184 of the suture anchor 180 and through one end 180a or 180b. The suture thread 182 is then knotted so as to remain generally fixed to the suture anchor 180. A free end of the suture thread 182 may be left free, or it may be combined with other suture threads 182, which are coupled to other suture anchors 180, and fed through a suture thread port 146 provided through the port element housing 116. The remaining length of the suture threads 182 may then reside in the hollow port cavity 118. If a plurality of suture threads 182 is provided, the free ends of the suture threads 182, that is, the ends of the threads 182 not coupled to the suture anchors 180, are preferably coupled in a pre-tied knot (186 in FIGS. 18-19).

To maintain some proximity of the needles 172 to the cannula shaft 150, each needle 172 may be at least partially covered by a needle guide 159. Such needle guide 159 may be provided as a needle sheath 160 as shown, or may be provided as a simple U-shaped retainer (not shown) provided over the needle 172 and anchored to the cannula shaft 150 at a desired location along its length 158. Furthermore, the needles 172 may reside in a longitudinal recessed groove (not shown) below the outer surface of the cannula shaft 150. For each needle 172 to be used, there is provided a flaring port 162 extending radially into the cannula throughbore 156 from external the cannula shaft 150. Located distally from the flaring port 162 is a needle fairing 164. The needle fairing 164 is adapted to reduce or prevent tissue contact with the needles 172 upon insertion of the trocar system 12 into a bodily organ. The needle fairing 164 slopes radially outwardly from the cannula shaft 150 from its distal end 164a to its proximal end 164b. Other components may be provided as a part of the cannula assembly 100. For instance, the cannula assembly 100 may include an insufflation port 140 in fluid communication with the open distal cannula end 152 and a cooperating stopcock 142 as is known in the art. Additionally, one or more retraction handles 144 may be coupled to or integrally formed with the port element housing 116.

FIG. 3 provides a further detailed view of the obturator assembly 200. The obturator assembly 200 generally includes an obturator housing 210 that at least partially contains a needle actuation mechanism 250. The obturator housing 210 preferably includes an obturator handle 212 coupled to an obturator shaft 214, which extends axially from the obturator handle 212, terminating at a pointed tip 216. The obturator handle 212 is preferably generally substantially cylindrical in shape, including at least one gripping element 213, such as a plurality of longitudinal grooves 215 formed in its outer circumferential surface 217. The obturator handle 212 also includes a top surface 212a and a bottom surface 212b and a throughbore 212c extending therethrough. Axially extending from the bottom surface 212b of the obturator handle 212 is the obturator shaft 214. Also extending from the bottom surface 212b of the obturator handle 212 is a rotational guide peg 219. The shaft 214 is preferably at least substantially cylindrical along a majority of its length 218, and includes a reentrant bore 220 formed therein and preferably situated coaxial to the throughbore 212c of the obturator handle 212.

The needle actuation mechanism 250 generally includes a control rod 252 extending between a first end 252a and a second end 252b. The control rod 252 is adapted to extend through the throughbore 212c of the obturator handle 212 and into the reentrant bore 220 of the obturator shaft 214. At the first end 252a of the rod 252, a control rod handle 254 is preferably provided, including a dimpled top surface 256 and a generally frustoconical bottom surface 258. The second end 252b of the rod 252 is preferably at least slightly tapered. Extending radially from the control rod 252 is at least one but preferably two yokes 260, which are adapted to cooperate with the needle engagement ring 174. Each yoke 260 includes at least an upper arm 262 that extends a first distance from the control rod 252. Each yoke 260 further preferably includes a lower arm 264 separated from the upper arm 262 by a ring channel 266. The lower arm 264 extends radially from the control rod 252 a second distance, which is preferably shorter than the first distance of the upper arm 262. If provided with an upper arm 262 and a lower arm 264, the arms are preferably spaced from each other by at least the width 176 of the needle engagement ring 174. The yokes 260 extend through a longitudinal yoke slot 268 provided through the wall of the obturator shaft 214. A control rod cover (not shown) may be provided so as to substantially cover the portion of the control rod 252 extending proximally from the obturator handle 212. The rod cover (not shown) may be removably coupled with the cannula housing 116 so as to provide an area of increased surface area over which the palm of the hand of a user may be placed during insertion.

Also supported as components of the obturator assembly 200 are a needle flaring mechanism 270 and a trocar position indication mechanism 290. The needle flaring mechanism 270 generally comprises a flaring wing 272 for each needle 172 provided on the needle assembly 170. Each flaring wing 272 is preferably generally L-shaped, including an upper leg 272a and a lower leg 272b, and preferably includes a tip portion 272c coupled to or formed as a part of the lower leg 272b. Each flaring wing 272, or a portion thereof, is extendable radially outward from the obturator shaft 214, preferably through a wing port 274 that is disposed in the shaft 214. While other arrangements are possible, it is preferred to have each flaring wing 272 pivotally supported in relation to the obturator shaft 214, such as by a wing pin 276 extending through the wing upper leg 272a, the wing pin 276 being supported by the shaft 214. Each wing 272 is preferably biased radially inward to the shaft 214. Where more than one wing 272 is used, the bias is preferably provided by a wing biasing band 278 that may be disposed about the wings 272, such as at the juncture of the upper leg 272a and lower leg 272b. Alternatively, if only one needle 172 and one wing 272 are used, a resilient biasing member (not shown) may be disposed between the upper leg 272a and the wall of the obturator shaft 214.

The trocar position indication mechanism 290 may include a resiliently biased wedge 292 and a wedge retractor 294. As can be more plainly seen in FIG. 11B, the wedge 292 preferably includes a proximal end 292a, a distal end 292b, and converging front 292c and back 292d sides. The wedge 292 may be pivotally supported near its distal end 292b by a wedge pin 293 that is supported by the obturator shaft 214. At the back side 292d of the wedge 292, a retraction plate 295 is disposed preferably generally perpendicular to the wedge 292. The retraction plate 295 has a wedge bearing surface 295a that faces the front side 292c of the wedge 292. Between the retraction plate 295 and the wall of the obturator shaft 214, in the reentrant bore 220, a resilient wedge biasing member 296 is disposed. While the wedge biasing member 296 may be tailored to provide a predetermined biasing force against the wedge 292, the wedge biasing member 296 may be, for example, a hollow cylinder of neoprene material adhered to the obturator shaft 214. The wedge retractor 294 is longitudinally slidably disposed within the reentrant bore 220, proximal to the wedge 292. The wedge retractor 294 may include two legs 294a, 294b separated by a wedge channel 294c. Each leg 294a, 294b includes a respective wedge retraction surface 297, which is adapted to slidably engage the wedge bearing surface 295a of the wedge retraction plate 295 as the legs 294a, 294b straddle the wedge 292.

In addition to or instead of the trocar position indication mechanism 290, the trocar system 12 may include other position indicia. For instance, the cannula shaft 150 may be provided with depth markers 151 indicating the depth of the most distal portion of the cannula shaft 150 relative to a reference tissue or organ. Furthermore, the needle actuation mechanism control rod 252 may be provided with needle extension markers 251 to indicate the position of the rod 252 with respect to the obturator handle 212.

FIG. 4 depicts the obturator assembly 200 being inserted into the cannula assembly 100 in a first longitudinal direction 502, the tip 216 having been inserted into the open proximal port end 112 of the cannula assembly 100. Generally, the yokes 260 are lined up with the yoke channels 126 and the rotational guide peg 219 may be aimed towards a preferred position in the rotational guide slot 122. Thus, the yokes 260 and the guide peg 219 generally form a key, thereby preventing, or at least hindering, erroneous insertion of the obturator assembly 200 into the cannula assembly 100. The obturator assembly 200, likely guided by the obturator handle 212, is inserted in the first longitudinal direction 502 a predetermined distance, such as until the obturator handle 212 or the rotational guide peg 219 or both contact the port element housing 116. After the obturator assembly 200 is inserted the predetermined distance, the trocar system 12 is in an inserted, but disengaged state.

FIGS. 5A, 5B, and 5C depict the trocar system 12 in an inserted, disengaged state. As can be seen, the pointed tip 216 of the obturator shaft 214 has passed through the entire cannula throughbore 156 provided in the cannula assembly 100. In this position, the rotational guide peg 219, if used, may be situated at a desired location along the rotational guide slot 126, and the upper arms 262 of the yokes 260 of the needle actuation mechanism 250 have engaged the needle engagement ring 174 adjacent the thin-walled portions 175a. Towards the distal end of the device 12, the trocar position indication mechanism wedge 292 may not yet be activated. That is, the wedge 292 preferably remains biased substantially within the obturator shaft 214, against the resilient wedge biasing member 296, by the cannula shaft 150 and a part of the planar ellipse 153 formed at the open distal cannula end 152.

FIGS. 6A, 6B, 6C, 7A, and 7B depict the trocar system 12 in an inserted, engaged state, the obturator handle 212 having been rotated in a first rotational direction 504. Once the obturator handle 212 has been rotated through a desired angle, such as the guide slot angle 124 provided by the rotational guide slot 122, the yokes 260 are engaged with the thick-walled portions 175b of the needle engagement ring 174, the ring 174 lying in the ring channels 266. Slight rotational frictional resistance is provided against the needle engagement ring 174 by the annular friction ring 177, so as to aid in the rotational engagement of the yokes 260 with the ring 174. Towards the distal end of the device 12, the trocar position indication mechanism wedge 292 may now be activated. That is, the wedge 292 is biased outwardly 506 by the wedge biasing member 296 such that the proximal end 292a protrudes radially beyond the cannula shaft 150. Thus, in the inserted, engaged state, the second end 252b of the control rod 252 is positioned generally proximal to the needle flaring mechanism 270 and the trocar position indication mechanism 290. Also in the inserted, engaged state, any longitudinal movement of the control rod 252 will result in associated longitudinal movement of the needle engagement ring 174.

Figure 9:
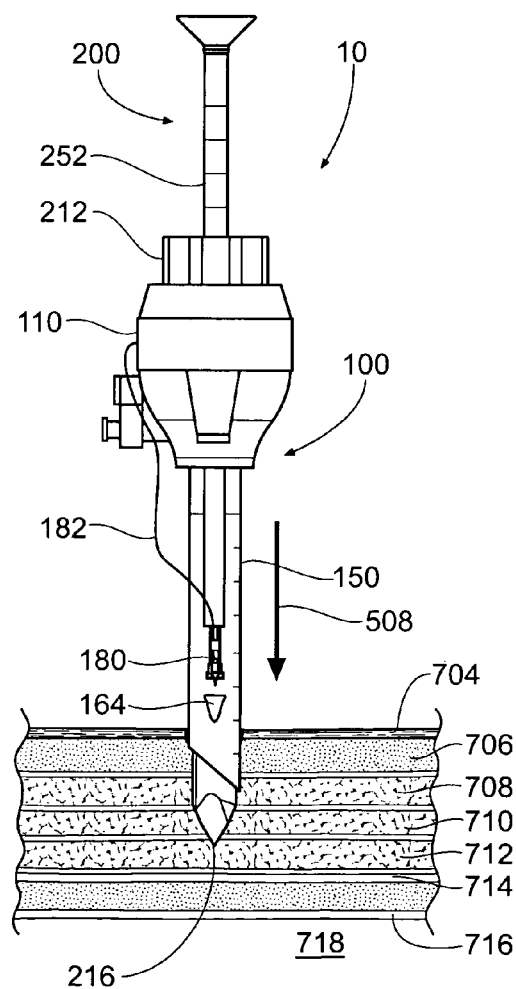
FIG. 9 is a right elevation view of a second step of a method according to the present invention.

The trocar system 12 may be inserted into an organ of a human body in either the inserted, disengaged state, or the inserted, engaged state, but the latter is preferred. FIGS. 8, 9, 10A, and 10B provide a right elevation view of the embodiment 10 being inserted into a portion of a human body. Although the example discussed will reference insertion into the abdomen of a patient, it is to be understood that similar insertions could be performed in any desirable organ of the body. In FIG. 8, an incision 702 has been made through the skin 704 of a human being. The trocar system 12 in its inserted and engaged state, is positioned at least substantially perpendicular to the skin surface, above the incision 702. The pointed tip 216 of the obturator shaft 214 is inserted into the incision 702, through the skin 704 and the superficial fascia 706. FIG. 9 depicts the obturator tip 216 and a portion of the cannula shaft 150 having been inserted in a second longitudinal direction 508 through the skin 704, the superficial fascia 706, an external oblique 708, an internal oblique 710, and into a transverses abdominus 712. As can be seen, radial pressure from the tissue generally overcomes the biasing force provided by the wedge biasing member 296 so as to force the wedge 292 at least substantially into the obturator shaft 214.

Figure 10A:
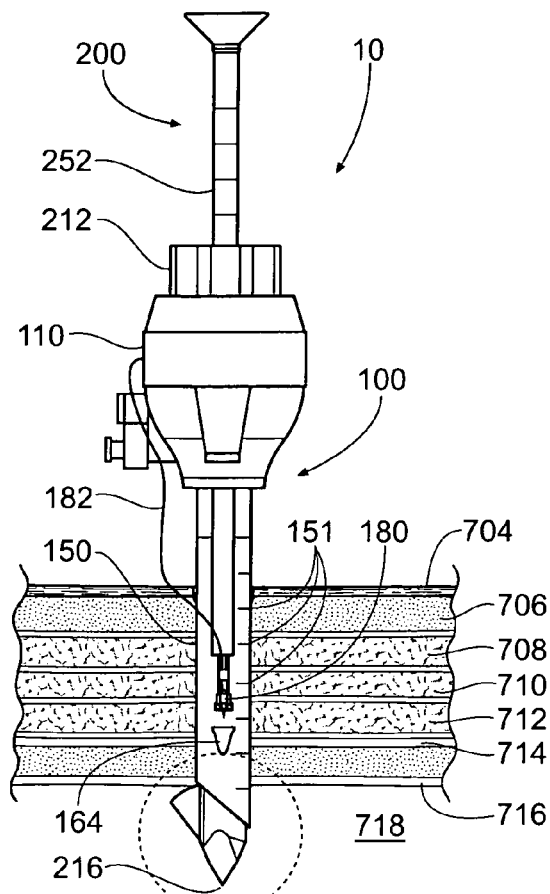
FIG. 10A is a right elevation view of a third step of a method according to the present invention.
Figure 10B:
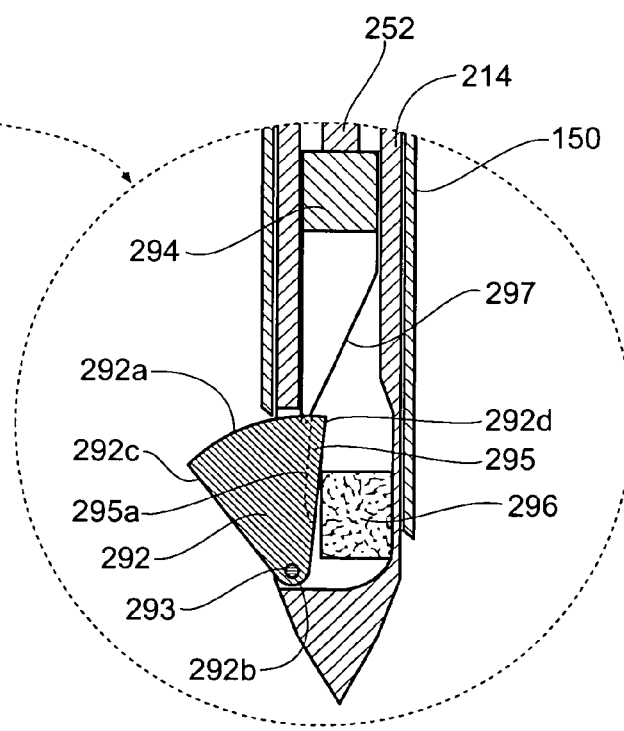
FIG. 10B is a right elevation cross-section view of the step of FIG. 10A.

The trocar assembly 12 continues to be inserted into a desired organ to a desired depth. FIG. 10A depicts the obturator tip 216 having penetrated a transversal is fascia 714 and parietal peritoneum 716, extending into an insufflated abdominal cavity 718. During insertion, the needle fairings 164 assist in attempting to prevent the needles 172 from being snagged by surrounding tissue. The proximal end 164b of the needle fairings 164 generally come to rest proximal to the organ into which the suture anchors 180 are to be deployed. In this case, the suture anchors 180 are to be deployed through the transversal is fascia 714 and the parietal peritoneum 716, extending at least partially into the insufflated abdominal cavity 718. Therefore, the proximal end 164b of the fairings 164 comes to rest proximal to, or superficial to, the fascia 714. In this position, the trocar position indication mechanism wedge 292 encounters decreased radial forces in the insufflated abdominal cavity 718. Thus, the wedge biasing member 296 is able to extend the wedge 292 radially outwardly, as shown in FIG. 10B. In this way, while depth may be indicated to a user of the device 10 by the depth markers 151 provided on the cannula shaft 150, a tactile indication is provided by the resistance to retraction of the device from the organ by the proximal end 292a of the wedge 292 contacting, in this case, the peritoneum 716.

Figure 11A:
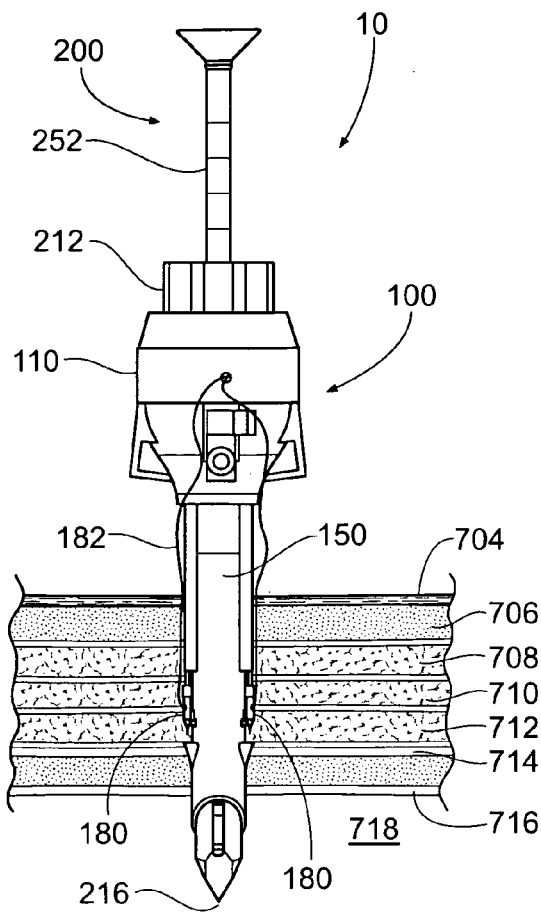
FIG. 11A is a front elevation view of the step of FIG. 10A.
Figure 11B:
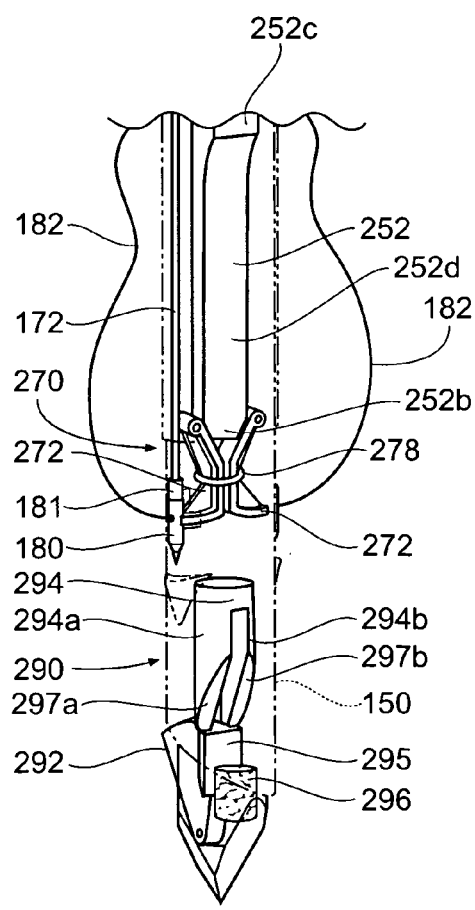
FIG. 11B is a partial cut-away view of the embodiment of FIG. 11A.

In this position, with desired tissue situated preferably between the proximal end 164b of the needle fairings 164 and the proximal end 292a of the wedge 292, the suture anchors 180 may be deployed. FIG. 11A is a front elevation view of the embodiment 10 inserted to the desired depth, as in FIG. 10A. FIG. 11B depicts a preferred relative positioning of the control rod 252, the needle flaring mechanism 270 and the trocar position indication mechanism 290 prior to deployment of the suture anchors 180. In this pre-deployment position, the control rod 252 is located proximal to a majority of the needle flaring mechanism 270, the second end 252b poised to engage the flaring wings 272.

Figure 12A:
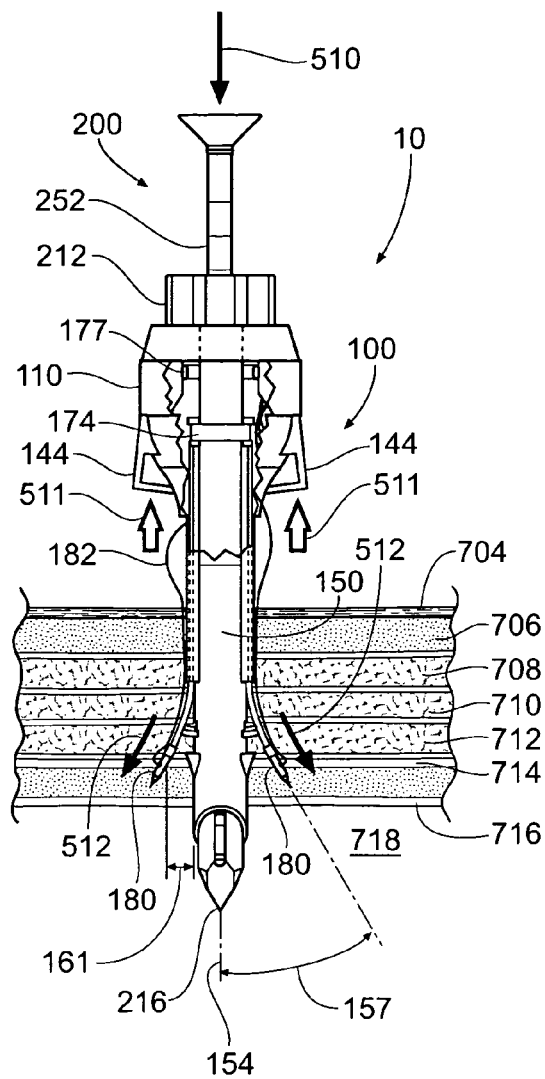
FIG. 12A is a front elevation view of a fourth step of a method according to the present invention.
Figure 12B:
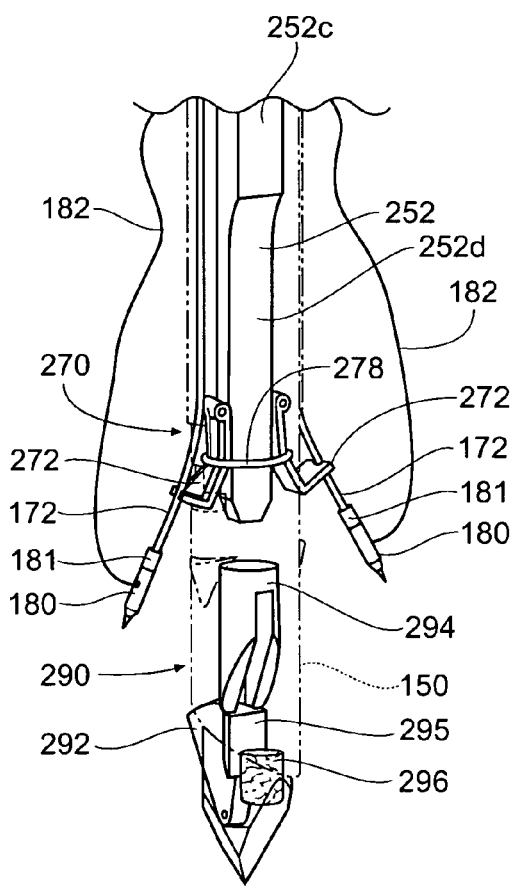
FIG. 12B is a partial cut-away view of the embodiment of FIG. 12A.

Deployment of the suture anchors 180 is commenced by movement of the control rod 252 in a third longitudinal direction 510, as seen in FIG. 12A, where the device 10 is in a mid-deployment position. The third longitudinal direction 510 may be at least substantially parallel to the second longitudinal direction 508. Force applied to the control rod 252 in the third longitudinal direction 510 may be counteracted by a substantially opposing force in a fourth longitudinal direction 511 placed on the retraction handles 144 of the port element 110. In this manner, the depth of the cannula assembly 100 may remain relatively constant. In this position, the control rod 252 has activated the needle flaring mechanism 270, but has not yet retracted the trocar position indication wedge 292. The needle flaring mechanism 270 is activated by the control rod 252 sliding between the needle flaring wings 272, thereby forcing the wings 272 radially outwardly against the needles 272, thus flaring the needles 172 away from the cannula shaft 150. That is, although the wings 272 are biased inwardly with respect to the cannula shaft 150, preferably by the wing biasing band 278, the control rod 252 overcomes such biasing effect to force the wings 272 outward. As shown, the wings 272 have been flared to their maximum extension, thereby guiding the needles 172 to enter the fascia 714 at a needle entry angle 157, which is preferably between about ten degrees and about forty-five degrees, more preferably between about twenty-five and about thirty-five degrees, and even more preferably about twenty-eight degrees. Also, the wings 272 help direct the needles 172 to a needle entry point in the organ to be pierced, in this case the fascia 714, that is spaced a preferred needle bite distance 161 from the outer surface of the cannula shaft 150. The needle bite distance 161 is preferably at least about five millimeters and is more preferably at least about 7.5 millimeters. As can be seen in FIG. 12B, the control rod 252 preferably has an area 252d of reduced thickness extending proximal from its distal, or second, end 252b. The area 252d allows a portion of the control rod 252 to slide within an aperture created by the wing biasing band 278 as the wings 272 are spread radially outward. Of course, rather than have an area of reduced thickness 252d, the entire control rod 252 may be shaped so as to allow for such passage.

Figure 13A:
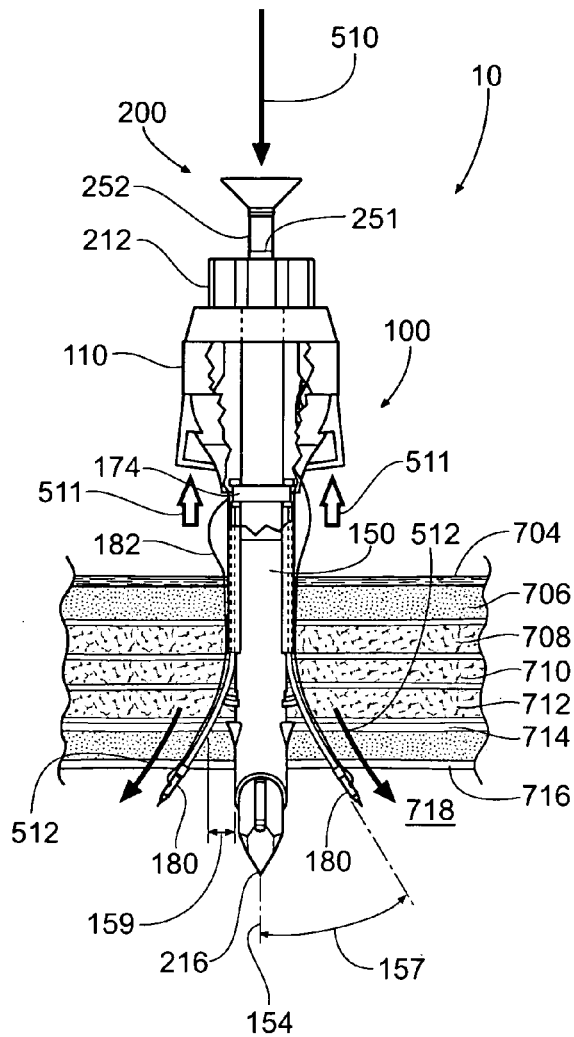
FIG. 13A is a front elevation view of a fifth step of a method according to the present invention.
Figure 13B:
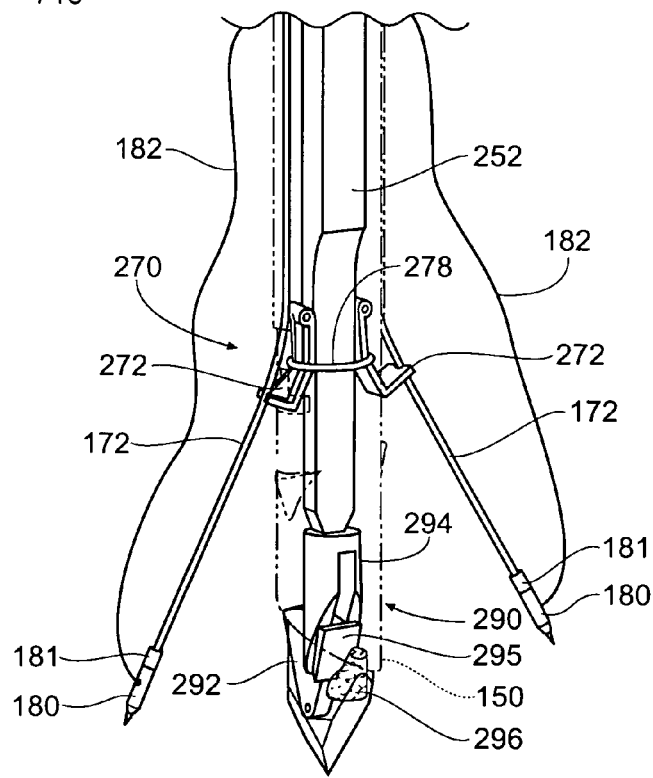
FIG. 13B is a partial cut-away view of the embodiment of FIG. 13A.

The deployment of the suture anchors may then be continued. As shown in FIG. 13A, the control rod 252 may continue to travel in the third longitudinal direction 510 for a desired distance, forcing the needles 172 in a needle direction 512. The distance may be physically limited, such as by the control rod handle 254 being interrupted by contact with the obturator handle 212, or by the yokes 260 abutting the end of the longitudinal yoke slots 268 provided in the obturator shaft 214. Alternatively, the distance may be determined by the needle extension markers 251 provided on the control rod 252, and manually limited. In the present example, the needles 172 have been extended so as to place the suture anchors 180 into the insufflated abdominal cavity 718. In the fully extended state, the control rod 252 has both activated the needle flaring mechanism 270 and also caused the retraction of the trocar position indication mechanism wedge 292. The retraction of the wedge 292 is caused by the control rod 252 forcing the wedge retractor 294 longitudinally distally, thereby causing the wedge retraction surfaces 297a, 297b of the wedge retractor legs 294a, 294b to slide across and frictionally engage the wedge bearing surface 295a. Thus, the biasing force of the wedge biasing member 296 is overcome and the wedge 292 is withdrawn into the obturator shaft 214.

Figure 14A:
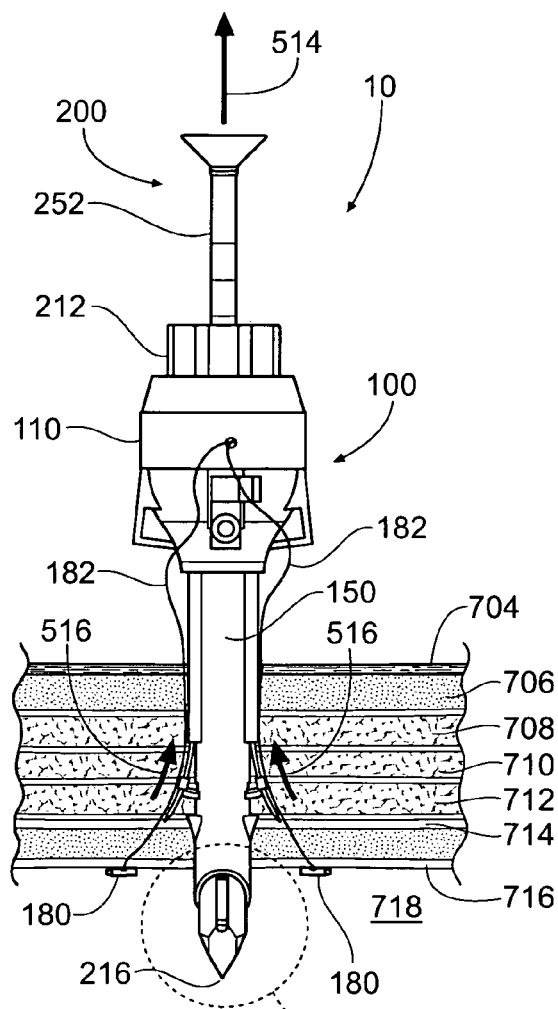
FIG. 14A is a front elevation view of a sixth step of a method according to the present invention.
Figure 14B:
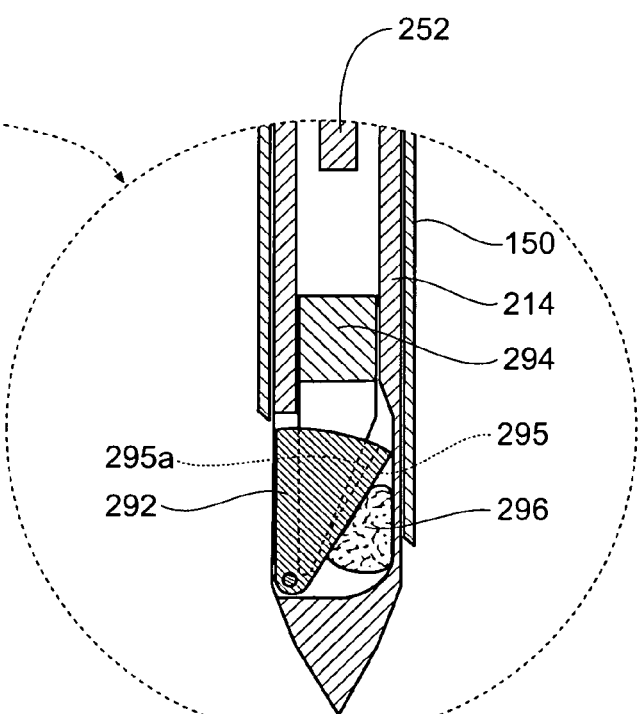
FIG. 14B is a left elevation cross-section view of the step of FIG. 14A.
Figure 15:
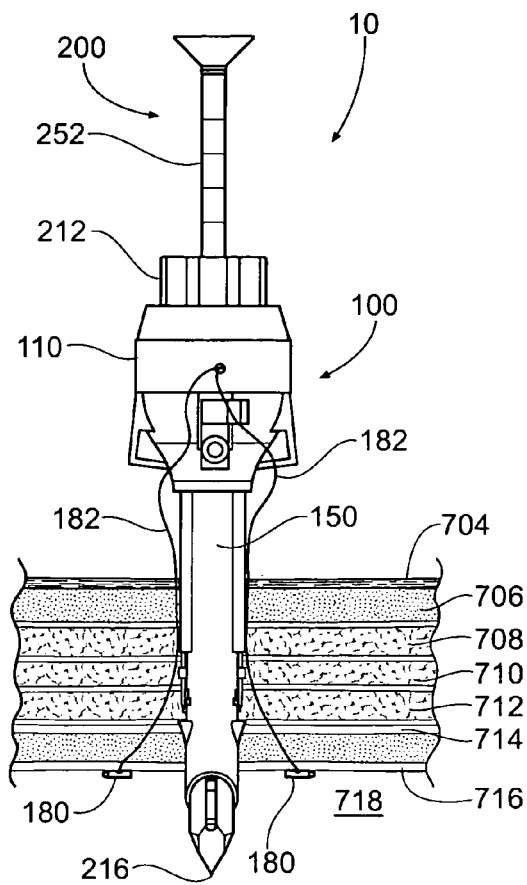
FIG. 15 is a front elevation view of a seventh step of a method according to the present invention.

As seen in FIG. 14A, to deposit the suture anchors 180, the needles 172 may be withdrawn in a reverse needle direction 516, which may be caused by moving the control rod 252 in a fifth longitudinal direction 514, such as by pulling on the bottom surface 258 of the control rod handle 254. As the control rod 252 is moved in the fifth longitudinal direction 514, the needles 172 are retracted, depositing the suture anchors 180 at a desired location. Furthermore, the wedge retractor 294 remains frictionally engaged with the wedge retraction plate 295 so as to maintain the wedge 292 in its retracted position, substantially within the obturator shaft, as shown in FIG. 14B. FIG. 15 shows the needles 172 having been retracted to their starting position and the suture anchors having been deposited in the insufflated abdominal cavity 718.

Figure 16:
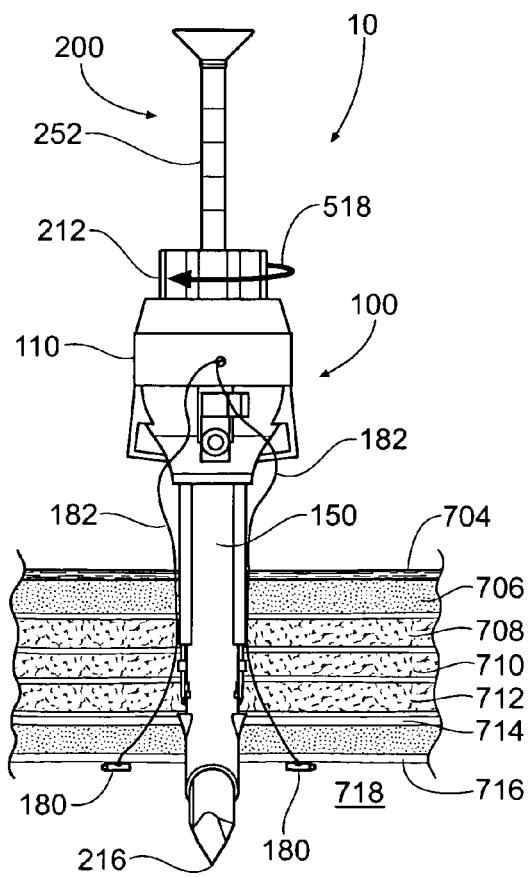
FIG. 16 is a front elevation view of an eighth step of a method according to the present invention.

Upon deposit of the suture anchors 180, it may be desirable to perform certain laparoscopic surgical procedures. If such is the case, the obturator assembly 200 may be removed from the cannula assembly 100, so as to provide the port element 110 as an access point for the laparoscopic procedure. FIG. 16 and FIG. 17 show the obturator assembly 200 being removed from the cannula assembly 100. The obturator handle 212 may be rotated in a second rotational direction 518, which may result in disengagement of the yokes 260 from the thick-walled portions 175b of the needle engagement ring 174 of the needle assembly 170. The obturator assembly 200 may then be moved in a sixth longitudinal direction 520, thereby withdrawing the obturator shaft 214 from the cannula assembly 100. The obturator assembly 200 may then be set aside. As shown in FIG. 18, the port element 100 may remain in place, thereby providing a laparoscopic portal through the open proximal port end 112 and the open distal cannula end 152. The suture threads 182 may be left in the port element housing 116, or they may be removed before, during or after the laparoscopic procedure, or may never have resided in the port element housing 116 at all.

Figure 19:
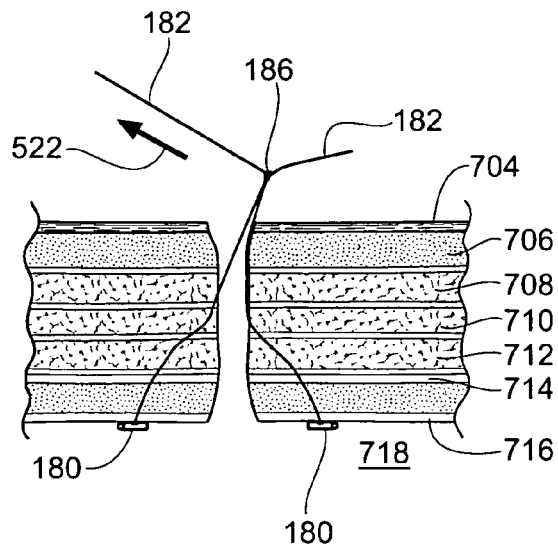
FIG. 19 is a front elevation view of an eleventh step of a method according to the present invention.
Figure 20:
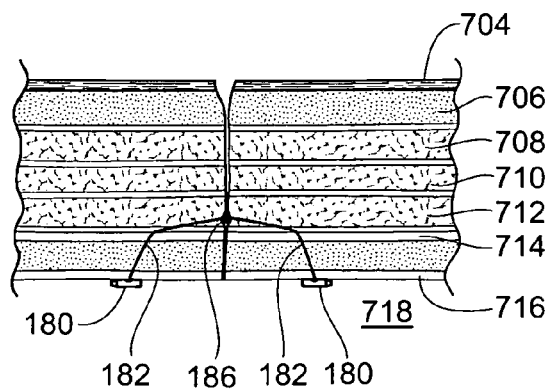
FIG. 20 is a front elevation view of a twelfth step of a method according to the present invention.

After the desired laparoscopic procedure, if any, the cannula assembly 100 may be removed from the body. FIG. 19 shows the portion of the body into which the cannula assembly 100 was positioned, but has been removed. The suture threads 182 are preferably provided with a pre-tied knot 186, which may be tightened by pulling one or more of the threads 182 in a suture tightening direction 522. When tightened, as shown in FIG. 20, the suture threads 182, in combination with the suture anchors 180, have successfully closed an opening in the bodily organ, which in this case includes the parietal peritoneum 716 and the fascia 714. The incision 702 in the skin 704 may then be closed using standard procedures such as suturing procedures.

Although the embodiment described may be used in conjunction with laparoscopic procedures, it may be desirable to provide an embodiment of a system according to the present invention for natural orifice surgery (NOS). While the embodiment 10 described could be used for NOS, an alternative embodiment may be provided where the needle actuation mechanism 250 is inseparable from the needle assembly 170, except upon destruction of the device. In such case, the obturator shaft 214 and the cannula shaft 150 may be formed integrally, such as in the form of a substantially unitary housing, thereby preventing withdrawal of the obturator assembly 200 from the cannula assembly 100. Additionally, the obturator handle 212 may also be integrally formed with the port element housing 116, and the needle engagement ring 174 may even be formed integrally with the control rod 252. If the needle engagement ring 174 is integrally formed or otherwise permanently affixed to the control rod 252, the annular friction ring 177 may be eliminated.

The various components of the present invention can be made from any materials suited for the purpose that the respective components serve. For instance, most of the components of the cannula assembly 100, including the port element housing 116, the insufflation port 140, the retraction handles 144, the cannula shaft 150, the needle guide 159, and the needle fairings 164 may all be formed from molded polycarbonate or other suitable plastic material. Additionally, most of the components of the obturator assembly 200, including the obturator handle 212, obturator shaft 214, control rod 252, yokes 260, needle flaring wings 272, trocar position indication wedge 292, and wedge retractor 294 may also be formed from molded polycarbonate or other suitable plastic material. Other materials, such as stainless steel, may be used, as well. Regarding the needle assembly 170, the needles 172 are preferably solid, extruded stainless steel, while the needle engagement ring 174 is preferably formed from molded polycarbonate or other suitable plastic material. The suture anchors 180 are preferably formed from a material, known in the art, which will break down or dissolve completely within a human body. The suture anchor stop 181 may be formed from any suitable material and coupled to the needle 172, or may be formed as a part of the needle 172. An exemplary material for the suture anchor stop 181 is adhesive lined heat shrinkable tubing. The suture thread 182 may also be formed from a material that is bioabsorbable, as such material is known in the art of suturing generally. In addition to plastic and metal, some resilient components, including the annular friction ring 177, the wing biasing band 278 and the wedge biasing member 296, may be formed from elastomeric materials.

The foregoing is considered as illustrative only of the principles of the invention. Furthermore, since numerous modifications and changes will readily occur to those skilled in the art, it is not desired to limit the invention to the exact construction and operation shown and described. For instance, it is to be noted that the various components of an embodiment of the present invention each may be constructed separately and then mechanically coupled, or the components may be formed each as unitary members. While the preferred embodiment has been described, the details may be changed without departing from the invention, which is defined by the claims.

We claim:

1. A system for deploying a suture anchor, said system comprising:
    a cannula assembly comprising:
        a port element defining an open proximal port end, said port element having a distal portion opposite said proximal port end;
        a cannula shaft extending from said distal portion of said port element to an open distal cannula end;
        a first needle at least partially longitudinally movable with respect to, and disposed at least partially radially external to, said cannula shaft; and
        a first suture anchor removably coupled to said first needle;
    a needle actuation mechanism at least partially longitudinally movable with respect to said cannula shaft; and an obturator assembly comprising an obturator housing including an obturator shaft at least partially insertable into and completely removable from said open proximal port end, wherein a portion of said needle actuation mechanism extends into said obturator shaft, wherein a first longitudinal movement of said needle actuation mechanism results in a corresponding second longitudinal movement of at least a first portion of said first needle.

2. A system according to claim 1, wherein said first suture anchor is passively removably coupled to said first needle.

3. A system according to claim 1, wherein said port element comprises a top surface at said open proximal port end, said top surface substantially surrounding a port aperture formed along a port longitudinal axis.

4. A system according to claim 3, wherein said port aperture is substantially circular in cross-section and further comprises a yoke channel extending radially therefrom.

5. A system according to claim 4, wherein said top surface further comprises a rotational guide slot formed about said port longitudinal axis through a guide slot angle.

6. A system according to claim 5, wherein said guide slot angle is about ninety degrees.

7. A system according to claim 5, said port element further comprising a port housing substantially surrounding a hollow port cavity.

8. A system according to claim 7, said port housing further comprising a pair of retraction handles.

9. A system according to claim 8, said port housing further comprising:
    an insufflation port in fluid communication with said port aperture;
    a stopcock operatively disposed to open and close said insufflation port; and
    a suture thread port in fluid communication with said hollow port cavity from external said housing.

10. A system according to claim 1, wherein said cannula shaft has a substantially circular cross-section formed about a cannula longitudinal axis along a majority of a cannula shaft length.

11. A system according to claim 10, said open distal cannula end comprising an ellipse formed in a plane provided at an acute ellipse angle measured distally from said open distal cannula end with respect to said cannula longitudinal axis.

12. A system according to claim 11, said ellipse angle comprising an angle of between about twenty degrees and about seventy-five degrees.

13. A system according to claim 11, said cannula shaft comprising a cannula throughbore formed through said cannula shaft length about said cannula longitudinal axis.

14. A system according to claim 13, said cannula assembly further comprising a flaring port extending radially outwardly from said cannula throughbore through said cannula shaft.

15. A system according to claim 14, said cannula shaft further comprising a first needle fairing disposed on an outer surface of said cannula shaft, said needle fairing sloping radially outwardly from said outer surface from a fairing distal end to a fairing proximal end.

16. A system according to claim 15, said cannula assembly further comprising a longitudinal needle sheath disposed on said cannula shaft, said sheath positioned substantially parallel to said cannula longitudinal axis.

17. A system according to claim 1, said system further comprising a needle flaring mechanism adapted to guide said first needle radially outwardly from said cannula shaft.

18. A system according to claim 1, said system further comprising a position indication mechanism.

19. A system according to claim 18, said position indication mechanism comprising:
    a wedge member pivotally mounted to said obturator shaft;
    a resilient wedge biasing member adapted to apply a wedge bias force to said wedge member forcing said wedge member radially outwardly from said obturator shaft;
    a wedge retractor adapted to selectively overcome the wedge bias force to retract said wedge at least substantially into said obturator shaft.

20. A system according to claim 19, said position indication mechanism further comprising a plurality of depth markers disposed on an outer surface of said cannula shaft.

21. A system according to claim 18, said position indication mechanism comprising a plurality of depth markers disposed on an outer surface of said cannula shaft.

* * * * *